United States Patent
Chin (10) Patent No.: US 10,799,609 B2
(45) Date of Patent: *Oct. 13, 2020

(54) APPARATUS AND METHOD FOR DETECTING MOISTURE IN A VACUUM CHAMBER

(71) Applicant: ASP Global Manufacturing GmbH, Schaffhausen (CH)

(72) Inventor: Han Chin, Corona, CA (US)

(73) Assignee: ASP GLOBAL MANUFACTURING GMBH, Schaffhausen (CH)

(*) Notice: Subject to any disclaimer, the term of this patent is extended or adjusted under 35 U.S.C. 154(b) by 200 days.

This patent is subject to a terminal disclaimer.

(21) Appl. No.: 15/914,793

(22) Filed: Mar. 7, 2018

(65) Prior Publication Data
US 2018/0193513 A1    Jul. 12, 2018

Related U.S. Application Data

(63) Continuation of application No. 15/151,774, filed on May 11, 2016, now Pat. No. 9,931,427.

(51) Int. Cl.
*A61L 12/08* (2006.01)
*A61L 2/20* (2006.01)
*A61L 2/24* (2006.01)

(52) U.S. Cl.
CPC .......... *A61L 12/084* (2013.01); *A61L 2/20* (2013.01); *A61L 2/208* (2013.01); *A61L 2/24* (2013.01);
(Continued)

(58) Field of Classification Search
CPC . A61L 9/20; A61L 2/0023; A61L 2/08; A61L 12/084; A61L 2/20; A61L 2/208
See application file for complete search history.

(56) References Cited

U.S. PATENT DOCUMENTS 4,551,311 A    11/1985 Lorenz
4,643,876 A    2/1987 Jacobs et al.
(Continued)

FOREIGN PATENT DOCUMENTS

CN    101065155 A    10/2007
CN    102423495 A    4/2012
(Continued)

OTHER PUBLICATIONS

"Technical Data Monograph: V-PRO® 1 Low Temperature Sterilization System and V-PRO® 1 Plus Low Temperature Sterilization System"; STERIS Corporate Document (Author Unknown); (2013).
(Continued)

*Primary Examiner* — Kevin Joyner
(74) *Attorney, Agent, or Firm* — Etan S. Chatlynne; Roberts Calderon Safran & Cole P.C.

(57) ABSTRACT

A method of operating a sterilization system having a vacuum chamber for sterilizing instruments, the chamber connected to a reservoir of sterilant by a valve in a closed state, is disclosed. The method may include taking a baseline humidity measurement while the pressure within the chamber is a first pressure, lowering the pressure within the chamber to a conditioning pressure, maintaining the conditioning pressure for a dwell time, increasing the pressure within the chamber, acquiring a second humidity measurement from within the chamber, and comparing the baseline humidity measurement to the second humidity measurement.

17 Claims, 5 Drawing Sheets

(52) U.S. Cl.
CPC ......... *A61L 12/086* (2013.01); *A61L 2202/24* (2013.01)

(56) References Cited

U.S. PATENT DOCUMENTS

| | | |
|---|---|---|
| 4,756,882 A | 7/1988 | Jacobs et al. |
| 5,317,896 A | 6/1994 | Sheth et al. |
| 5,445,792 A | 8/1995 | Rickloff et al. |
| 5,482,683 A | 1/1996 | Sheth et al. |
| 5,641,455 A | 6/1997 | Rosenlund et al. |
| 5,788,925 A | 8/1998 | Pai et al. |
| 5,872,359 A | 2/1999 | Stewart et al. |
| 5,961,922 A | 10/1999 | Witte et al. |
| 8,366,995 B2 | 2/2013 | McLaren et al. |
| 9,277,850 B2 | 3/2016 | Kubach |
| 10,441,672 B2 | 10/2019 | Truong et al. |
| 2008/0267818 A1 | 10/2008 | Hill |
| 2015/0313250 A1 | 11/2015 | Itarashiki et al. |

FOREIGN PATENT DOCUMENTS

| | | |
|---|---|---|
| WO | 2006/057523 A1 | 6/2006 |
| WO | 2007012866 A1 | 2/2007 |
| WO | 2007125100 A1 | 11/2007 |
| WO | 2008134290 A1 | 11/2008 |

OTHER PUBLICATIONS

Extended European Search Report for Application No. 17170503.1 dated 26 Jan. 1, 2018, 8 Pages.

Partial European Search Report for Application No. 171705031 dated Oct. 4, 2017, 10 Pages.

APPARATUS AND METHOD FOR DETECTING MOISTURE IN A VACUUM CHAMBER

REFERENCE TO RELATED APPLICATION

The present application claims the benefit under 35 U.S.C. § 120 as a continuation of U.S. patent application Ser. No. 15/151,774, filed on May 11, 2016, which is hereby incorporated by reference in its entirety.

FIELD

The subject matter disclosed herein relates to the detection of moisture in a chamber in which a vacuum is being drawn. It is particularly useful in chemical vapor sterilization techniques.

BACKGROUND

Medical devices may be sterilized before use in order to minimize the likelihood that a device contaminated by, e.g., microorganisms might be used on a subject, which could cause an infection in the subject. Various sterilization techniques may be employed, using sterilants including one or a combination of steam, ethylene oxide, chlorine dioxide, ozone, peracetic acid, and hydrogen peroxide. Often the chemical sterilants are employed in a gaseous and/or a plasma form. For these techniques, sterilization is typically conducted within a sterilization chamber of a sterilization system. For certain chemical sterilization techniques, such as those using hydrogen peroxide, the sterilization chamber typically includes a vacuum chamber that is not only capable of achieving low pressures therein, but of also introducing sterilants therein and withdrawing sterilants therefrom. Some chemical sterilization processes, such as those that use ethylene oxide, require water vapor within the vacuum chamber to be effective. However, for other chemical sterilization processes, such as those that use hydrogen peroxide, water in vapor, liquid, or solid form within the vacuum chamber may decrease effectiveness or cause the process to cancel.

A typical chemical vapor sterilization process for medical devices begins with medical-facility personnel preparing the devices for sterilization by washing the instruments with water and/or a washing solution to remove solids and liquids from the instrument. The personnel then dries the instruments, (e.g., using heat, medical-grade compressed air, and/or towels) and perhaps wraps them in a wrap suitable for sterilization, which acts as a barrier to microorganisms but that permits passage of a sterilant therethrough. Instruments wrapped in a wrap are sometimes referred to as a sterilization pack or load. The load is then placed into the vacuum chamber of the sterilization system and the chamber is closed (sealed), typically by closing the chamber's door. The chamber may be heated, which may help vaporize water that may be within the chamber. Next, the atmosphere in the chamber, which may include water vapor, is evacuated. In some sterilization procedures, air within the vacuum chamber may be excited to form an air plasma, which may further aid in vaporizing water for removal from the chamber. After achieving a low pressure, sometimes referred to as a vacuum or a rough vacuum, a sterilant is introduced into the chamber, either in gaseous or vapor form or as a mist that vaporizes in the low pressure environment of the chamber. The added gas in the chamber slightly raises the pressure in the chamber. The sterilant spreads throughout the chamber, entering small or confined spaces, such as cracks, crevices, and lumens in the medical devices contained therein. The sterilant bathes the medical devices, which kills bacteria, viruses, and spores disposed upon and within the devices that it contacts. In some sterilization procedures, particularly low-temperature procedures that utilize hydrogen peroxide, the hydrogen peroxide gas may be excited via an electric field to change the gas into a plasma. Finally, the sterilant is evacuated from the chamber and the chamber is returned to the ambient pressure. After the sterilization process has ended, the instruments may be removed from the chamber.

Typically, healthcare personnel check whether the sterilization process was efficacious using various techniques known in the art, e.g., by use of a self-contained biological sterilization indicator, such as the STERRAD® CYCLESURE® 24 Biological Indicator, manufactured by Advanced Sterilization Products, Division of Ethicon US, LLC, located in Irvine Calif. Confirmation using this biological indicator typically requires about twenty-four hours. During this time, while the effectiveness of the sterilization remains unconfirmed, medical personnel may decide not to use the medical devices. This may cause inventory management inefficiencies for a health care provider, such as a hospital, because, for example, the medical devices should be stored while they cannot be used, perhaps requiring the health care provider to keep more medical devices in its inventory than it otherwise would to ensure a sufficient supply of medical devices. Alternatively, health care providers may use the medical devices before the sterilization confirmation is completed and sterilization efficacy confirmed. However, using the medical devices before sterilization efficacy has been confirmed may expose a subject of a medical procedure to risk of infection from the medical devices. Given the total amount of time medical devices may be unsuitable for use because of the time required to conduct a sterilization process and the time required to confirm that the sterilization process was efficacious, healthcare personnel desire updated sterilization processes and confirmation techniques that require less time to conduct and reduce the likelihood that a process may fail as compared to those presently available.

An example of a commercially available sterilization chamber is the STERRAD® 100NX® System manufactured by Advanced Sterilization Products, Division of Ethicon US, LLC, located in Irvine Calif. The 100NX® is advertised as being capable of sterilizing most general surgical instruments in 47 minutes. The cycle temperature of the 100NX® is advertised as being between 47° C. to 56° C. These temperatures are preferred for helping to vaporize residual water with heat without over-heating the instrument, which could compromise the function or structure of instruments. Further, these temperatures are preferred for generating plasma, which helps improve the effectiveness of the sterilization process and further helps vaporize any residual water, and to aid in removing residual hydrogen peroxide from the vacuum chamber.

Commercially available sterilization systems that employ, e.g., hydrogen peroxide are designed to preferably operate without any residual water on loads in the sterilization chambers. Although some sterilization systems introduce hydrogen peroxide as a vapor mixed with water vapor into the sterilization chamber, generally, hydrogen peroxide should not be introduced into a chamber where moisture may be present. If healthcare personnel erroneously introduced water into the chamber on the load, the water will begin evaporating as the pressure within the chamber is lowered to maintain a surface-pressure equilibrium between the water and its surroundings. This pressure equilibrium, which is also a function of temperature, is typically referred to as the vapor pressure of water. At 100° C., the vapor pressure of water is one atmosphere, or 760 torr, which is why it is commonly stated that water boils at 100° C. However, when the local pressure around water is less than 760 torr, the liquid water may change phase to water vapor at lower temperatures.

Some sterilization systems check for the presence of water in the sterilization chamber before they introduce a sterilant gas therein based on analyses of pressure measurements taken within the chamber. For example, some check for small increases in pressure inside the chamber while vacuum is being drawn. If no water is present in the chamber while vacuum is being drawn, the pressure decreases asymptotically without any increases therein. However, if any water is in the chamber while vacuum is being drawn, at least some of the water may turn to vapor, which may cause slight local increases in pressure. Accordingly, detection of a small pressure increase while vacuum is being drawn indicates the presence of water in the vacuum chamber. Other sterilization systems lower the pressure in the chamber to a predetermined pressure level and then attempt to maintain the pressure at that predetermined pressure level while monitoring the chamber for pressure increases that may be attributable to water vapor.

Although the goal is to identify whether any moisture may be present within the chamber, pressure and not humidity is the quantity that is typically monitored to ensure adequate dryness of a vacuum chamber for hydrogen-peroxide based sterilization. Humidity sensors are sometimes used to confirm that required humidity levels are present in other types of sterilization, such as EtO sterilization, but in that context, moisture is required for EtO sterilization to be effective whereas in hydrogen peroxide sterilization, moisture should be avoided.

When water is detected during a hydrogen peroxide sterilization process, the process may be aborted so that excess water may be removed from the medical devices before attempting sterilization again. Aborting a sterilization process as soon as water is detected may help save time and resources as compared to continuing a sterilization process that may not be efficacious, and may help avoid use of a non-sterile device.

In some instances, instead of aborting the sterilization process, it may be preferable to attempt to remove the water from the vacuum chamber by a process called "load conditioning." Load conditioning is typically accomplished by, first, some combination of heating and/or introducing plasma into the sterilization chamber and re-pressurizing the sterilization chamber to transfer energy to the water, and, second, drawing a vacuum anew to convert the water to vapor. Load conditioning may occur before, after, or both before and after vacuum is drawn in the chamber. In some instances, load conditioning cannot remove water from the chamber. In other instances, load conditioning may remove some but not all of the water. In such instances, additional load conditioning may be attempted, which may ultimately remove sufficient moisture from the chamber.

SUMMARY

The disclosed subject matter concerns a sterilization system and methods of operating the sterilization system. In some embodiments, the sterilization system may have a vacuum chamber for sterilizing instruments that is connected to a reservoir of sterilant by a valve in a closed state. A first example method may include the steps of placing the instruments in a non-sterile state into a sterilization pack, opening the chamber, placing the pack into the chamber, placing a biological indicator into the chamber, closing the chamber, withdrawing a first volume of air from the chamber, changing a volume of liquid water into vapor, opening the valve, introducing a sterilant into the chamber, withdrawing the sterilant from the chamber, introducing a second volume of air into the chamber, opening the chamber, removing the pack from the chamber, and removing the instruments from the pack in a sterile state. The first example method may also include the steps of acquiring a baseline humidity measurement from within the chamber when the pressure within the chamber is a first pressure, lowering the pressure within the chamber to a conditioning pressure, maintaining the conditioning pressure for a dwell time, increasing the pressure within the chamber, acquiring a second humidity measurement from within the chamber; and comparing the baseline humidity measurement to the second humidity measurement.

A second example method of operating a sterilization system having a vacuum chamber for sterilizing instruments may include initiating a timer in a digital computer, acquiring a baseline humidity measurement from within the chamber, withdrawing a first volume of air from the chamber, repeatedly acquiring first subsequent humidity measurements from within the chamber while withdrawing the first volume of air from the chamber, waiting for a dwell time after the first volume of air is withdrawn from the chamber, repeatedly acquiring second subsequent humidity measurements from within the chamber during the dwell time, introducing a second volume of air into the chamber, repeatedly acquiring third subsequent humidity measurements from within the chamber while introducing the second volume of air, identifying, with the digital computer, a maximum humidity measurement from among the third subsequent humidity measurements, and comparing the maximum humidity measurement to another humidity measurement. The another humidity measurement may be the baseline humidity measurement. Alternatively, the another humidity measurement may be a minimum humidity measurement from among the first subsequent humidity measurements and second subsequent humidity measurements. In the second example method, the steps of acquiring the baseline humidity measurement, acquiring the first subsequent humidity measurements, acquiring the second subsequent humidity measurements, and acquiring the third subsequent humidity measurements may include repeatedly taking humidity measurement data with a humidity sensor and storing the data in a non-transitory storage medium of the digital computer. The second example method may also include the steps of automatically opening the chamber and removing the instruments in a sterile state from the chamber. The second example method may also include the step of closing the chamber, in which case the step of initiating the timer may occur after the step of closing the chamber. Additionally, the step of withdrawing a first volume of air from the chamber may begin after the step of initiating the timer. In the second example method, the maximum humidity measurement may be greater than the baseline humidity measurement. In this case, the second example method may also include the step of automatically commencing a sequence of vacuum pulsing. In the second example method, the maximum humidity measurement may be less than or equal to the baseline humidity measurement. In this case, the second example method may also include the step of automatically opening a valve connected to a sterilant reservoir after comparing the maximum humidity measurement to the baseline humidity measurement. In the second example method, the sterilant reservoir may contain hydrogen peroxide.

There sterilization set forth herein may include a variety of components and subsystems. For example, an example sterilization system may include a vacuum chamber, a vacuum pump, a first valve disposed between the vacuum chamber and the vacuum pump, a sterilant reservoir containing hydrogen peroxide, and a humidity sensor disposed adjacent to the vacuum chamber and configured to detect humidity within the vacuum chamber. The humidity sensor may be disposed upon the vacuum chamber. A second valve may be disposed between the vacuum chamber and the sterilant reservoir. A seal may be disposed between the vacuum chamber and the sterilant reservoir. The seal may include a sheet of metal or plastic. A third valve may be disposed between the vacuum chamber and the humidity sensor. The third valve may be configured to prevent hydrogen peroxide from contacting the humidity sensor. The humidity sensor may be a relative humidity sensor. A fourth valve may be disposed between the sterilant reservoir and the ambient environment. A fifth valve may be disposed between the vacuum chamber and the ambient environment.

BRIEF DESCRIPTION OF THE DRAWINGS

While the specification concludes with claims that particularly point out and distinctly claim the subject matter described herein, it is believed the subject matter will be better understood from the following description of certain examples taken in conjunction with the accompanying drawings, in which:

DETAILED DESCRIPTION

The following description sets forth certain illustrative examples of the claimed subject matter. Other examples, features, aspects, embodiments, and advantages of the technology should become apparent to those skilled in the art from the following description. Accordingly, the drawings and descriptions should be regarded as illustrative in nature.

I. A Sterilization System

Figure 1:
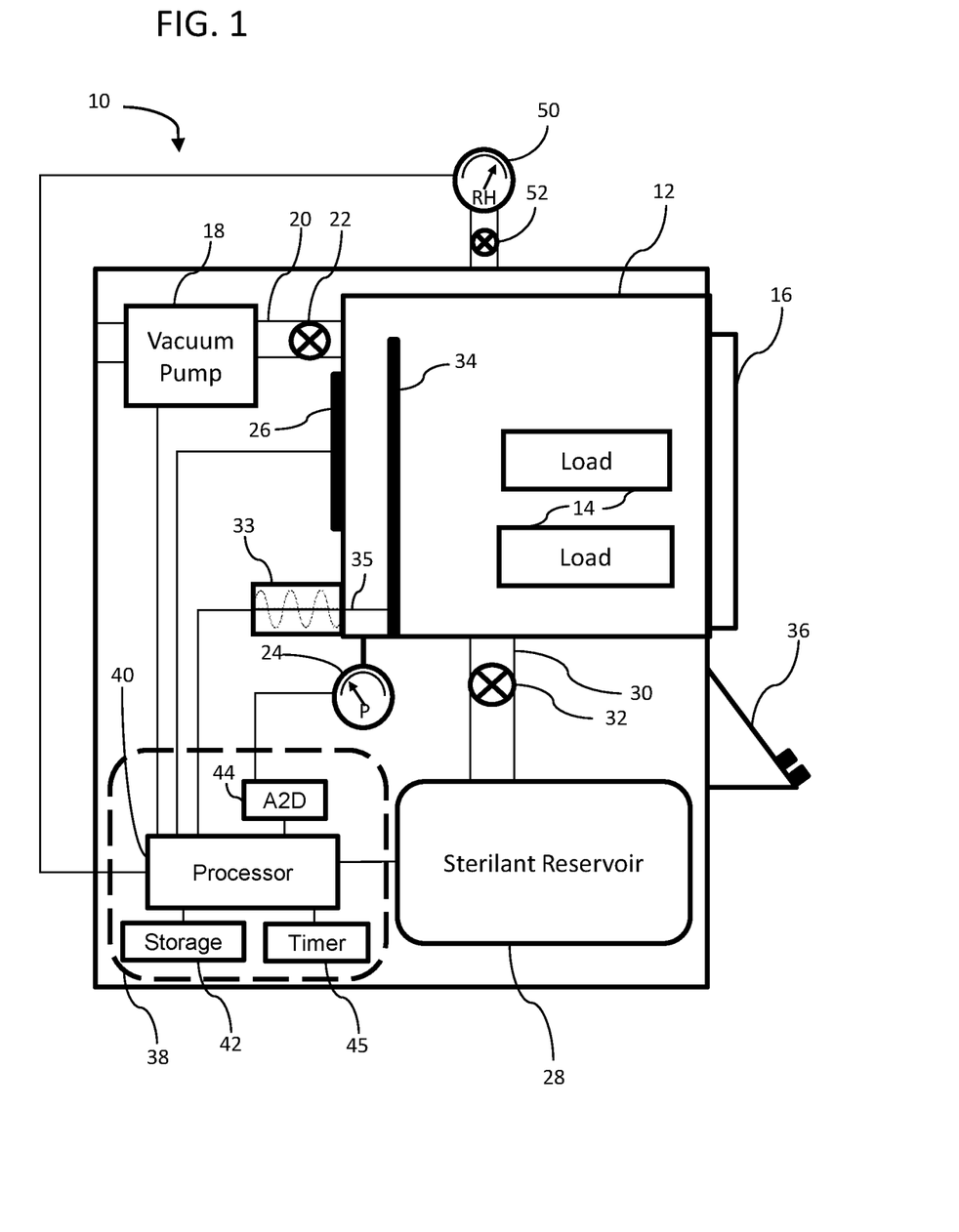
FIG. 1 depicts, in block diagram form, a sterilization system having a vacuum chamber that may be used to practice the methods disclosed herein.

FIG. 1 reflects a sterilization system 10, depicted schematically in block diagram-format. It comprises, a vacuum chamber 12 having a load (pack) 14 of instruments therein to be sterilized. The chamber 12 may be formed of any material that is sufficiently robust to handle pressures as low as approximately between 0.15 torr and 3 torr, and sufficiently inert to avoid reacting with or absorbing any sterilants introduced therein. Such materials may include aluminum and stainless steel. Chamber 12 may also include an openable and sealable barrier 16, such as a door, that may be opened to allow placement and removal of load 14 into chamber 12. The barrier should be sufficiently robust, and include a sufficiently robust seal, to withstand low pressures drawn within chamber 12 and avoid leaks between chamber 12 and the ambient environment. A vacuum pump 18 capable of reaching the desired operating pressure evacuates air and other gases, such as water vapor, from chamber 12. Vacuum pump 18 may include a hose or pipe 20 to connect it to chamber 12. Vacuum pump 18 may also include a valve 22, which may be opened or closed to assist or prevent pressure changes in chamber 12. For example, when the valve is open and the vacuum pump is operational, the pressure in chamber 12 may be lowered. Alternatively, when the valve is open and the vacuum pump is not operational, the pressure in the chamber may be equalized to the ambient pressure. In other embodiments, a venting valve may be used to vent or evacuate chamber 12 to introduce ambient air into chamber 12 and return the pressure within chamber 12 to the ambient pressure. This venting valve, which is not shown in FIG. 1, may be used instead of or in addition to pump 18 and valve 22 to adjust the pressure within chamber 12. A hose or pipe may connect chamber 12 to the ambient environment and the venting valve may be disposed within this hose or pipe between the ambient environment and chamber 12. A pressure monitor 24 monitors the pressure in chamber 12. Particularly suitable pressure monitors are capacitance manometers available from MKS Instruments. A heating element 26 may be used to heat the chamber 12. It may comprise separate elements bonded to the outside of the chamber 12 in locations sufficient to uniformly heat the chamber 12. A tank or reservoir 28 containing sterilant, which includes a hose or pipe 30, is connected to chamber 12. In some embodiments, tank 28 may further include a valve 32, which may be disposed between chamber 12 and tank 28 to control the flow of sterilant from tank 28 through hose 30 and into chamber 12. In some embodiments, in lieu of or in addition to valve 32, a seal may be disposed between tank 28 and hose or pipe 30. The seal may be opened, e.g., by puncturing, to permit the sterilant enter hose or pipe 30. Accordingly, the seal may be fabricated from, among other things, a sheet of metal or plastic, such as aluminum foil. Alternatively or additionally, another hose or pipe with a valve positioned therein may be disposed between tank 28 and the ambient environment to further aid in venting chamber 12 after sterilant has been introduced therein.

A power source and/or signal generator 33 and an electrode 34 disposed within chamber 12 may be provided to create an electric field within chamber 12 between electrode 34 and the interior surface of chamber 12 to create a plasma therein. A signal, such as an RF signal, may be provided to electrode 34 from generator 33 by way of a feed through 35, such as a wire-type feed through. Creation of a plasma is useful for low temperature sterilization processes that use hydrogen peroxide gas. In these processes, the hydrogen peroxide gas may be excited to form a hydrogen peroxide plasma. Alternatively, another gas may be used to form the plasma, such as air, which may help lower hydrogen peroxide residuals upon the load to facilitate removal of hydrogen peroxide from chamber 12. Sterilization system 10 may also include a user interface 36, that may include output devices, such as a printer or display, and user-input devices, such as a keypad or touch screen. Sterilization system 10 may also include a humidity or relative humidity sensor 50, such as the HIH-4602-A/C Series Relative Humidity sensor produced by Honeywell International, Inc. In some embodiments, a valve 52 is disposed between humidity sensor 50 and vacuum chamber 12 to shield sensor 50 from high concentrations of hydrogen peroxide, which could damage sensor 50. That is, valve 52 may be in an open state when hydrogen peroxide is not within chamber 12, thereby allowing sensor 50 to acquire humidity measurements of the air and/or gases within chamber 12. Valve 52 may be in a closed state when hydrogen peroxide is within chamber 12 and/or before hydrogen peroxide is introduced into chamber 12 from sterilant reservoir 28. When valve 52 is in a closed state, sensor 50 is sealed off from chamber 12 and any hydrogen peroxide therein, thereby protecting sensor 50 from being damaged by hydrogen peroxide.

A control system 38, such as a digital computer, controls the operation of the system 10 and its various components. Control system 38 may employ one or more microprocessors 40. It may also employ a non-transitory storage medium 42, such as random access memory (RAM), a hard-disk drive, or flash memory, which can store data, such as pressure values, humidity values, and time values. An analog to digital (A2D) converter 44 may be used to convert analog data to digital data if analog data, such as pressure data and/or humidity data, is collected. A timer or clock circuit 45 keeps time. Control system 38 may further include software and/or logic by which the microprocessor may determine maximum or minimum values from among the pressure data and/or humidity data. Control system 38 may further include software and/or logic by which the microprocessor may compare pressure and/or relative humidity values to other pressure and/or relative humidity values. For example, the control system is capable of storing pressure data $P_i$ and humidity data, $H_i$ which are acquired at various time increments i. The amount of time between neighboring time increments, designated $\Delta t$, may be equal to approximately 0.1 second, approximately 1 second, approximately 2 seconds, approximately 5 seconds, or approximately 10 seconds. The pressure data and relative humidity data may be measured throughout the sterilization process and stored in storage medium 42. The data may be collected as voltage outputs from the corresponding pressure or relative humidity sensor.

II. Determining Moisture Content

Ideally, load 14 is introduced into chamber 12 completely dry, i.e., without any moisture thereon. In some instances, particularly where the instruments to be sterilized are not sufficiently dried by healthcare personnel, residual water may be introduced into the vacuum chamber. In these instances, water may be in chamber 12 when the vacuum draw of the sterilization process commences, i.e., when vacuum pump 18 is activated. As the pressure in the chamber decreases, at least a partial volume of the residual water may change phase to gas, which may interfere with a sterilization process, such as a hydrogen peroxide sterilization process. Further, at least a partial volume of any residual water that does change phase to gas may change phase to ice. Hydrogen peroxide may condense on this ice and prevent hydrogen peroxide from contacting the device underneath the ice, thereby further decreasing the efficacy of the sterilization process.

Although the prior art includes examples of identifying moisture in a vacuum chamber via pressure measurements and basing a determination of whether to proceed with a hydrogen peroxide sterilization process based on an analysis of these measurements, the inventors are unaware of any such determinations being based upon an analysis of humidity or relative humidity measurements. Previously, humidity-based determinations were believed to be inadequate because of the difficulty humidity and/or relative humidity sensors have detecting water-vapor molecules in vacuum chambers at low pressures appropriate for hydrogen peroxide sterilization. That is, when pressure within a vacuum chamber is lowered from, e.g., approximately atmospheric pressure to a pressure of, e.g., approximately 10 torr, the water-vapor molecules that remain in the chamber or that are generated via vaporization do not contact the humidity sensor sufficiently to generate an output from the sensor that accurately represents the moisture content in chamber 12. Accordingly, it has been believed that humidity data should not be used to assess moisture content within a vacuum chamber as a basis for a determination of whether to introduce hydrogen peroxide therein.

The inventors have discovered a surprising mechanism by which a humidity or relative humidity sensor may be used to measure moisture content within a vacuum chamber such that the measurements may form a basis for determining whether hydrogen peroxide should be introduced into the chamber for the purpose of sterilization. Set forth herein is a new, useful, and inventive application of this discovery, which improves sterilization processes and load-conditioning techniques known in the art.

In some embodiments, the starting pressure in chamber 12 is equal to or approximately equal to the ambient pressure, e.g., atmospheric pressure. Chamber 12 may be sealed by closing barrier 16. Humidity or relative humidity sensor 50 is used to take a baseline reading of the humidity within chamber 12. Then, air may be withdrawn from chamber 12 by opening valve 22 of vacuum pump 18 and activating the pump to lower the pressure in chamber 12 to a conditioning pressure, $P_c$, of between approximately 5 to approximately 15 torr, approximately 8 torr to approximately 12 torr, or approximately 10 torr. Valve 22 may then be closed and pump 18 deactivated in order to maintain the pressure within chamber 12 at $P_c$ or approximately $P_c$ for a period of time to allow residual water in load 14 to vaporize. Vaporization may be assisted by activating heating elements 26. The period of time, or dwell time, $t_d$, during which valve 22 is closed to maintain pressure may be between approximately 1 second to approximately 5 minutes, approximately 1 second to approximately 1 minute, approximately 1 second to approximately 50 seconds, approximately 1 second to approximately 10 seconds, or approximately 5 seconds. Time may be monitored by timer 45 and each time increment $\Delta t$ corresponding to each humidity measurement may be stored in non-transitory storage medium 42. Correspondingly, throughout the process or a portion thereof, humidity or relative humidity sensor 50 measures the humidity at each time increment $\Delta t$, and the output of sensor 50, typically a voltage output, is also recorded in nontransitory storage medium 42.

After the dwell time has passed, chamber 12 is pressurized. For example, valve 22 and/or the venting valve may be opened to allow ambient air into chamber 12. As air enters or rushes into chamber 12, this air and any water vapor in the chamber mix and, as the inventors discovered, this activity brings water molecules within chamber 12 into contact with the humidity sensor. If any residual water was introduced into vacuum chamber 12 when load 14 was disposed therein, introduction of air having the same moisture content as the air that was drawn out of chamber 12 causes the overall moisture content within chamber 12 to be greater than what it was originally. That is, the moisture content within chamber 12 should be higher than the baseline moisture content as determined by humidity sensor 50.

For example, in one embodiment, the process begins with ambient air in chamber 12. Hospital personnel dispose load 14 therein, but with a volume of residual water within the load because the load was not sufficiently dried. The pressure in chamber 12 is lowered to a conditioning pressure of approximately 10 torr, valve 22 is then closed, and the pressure maintained at approximately at the conditioning pressure for a dwell time of approximately 0.1 seconds, 1 second, 5 seconds, or 10 seconds. From approximately the time at which the pressure in chamber 12 started being lowered, at least some of the molecules of the residual water vaporize. Valve 22 or the venting valve is then opened to pressurize and/or vent chamber 12. This causes, e.g., ambient air to mix with the air inside the chamber, which has a higher water-vapor content than the ambient air because some of the residual water on load 14 should have vaporized. This mixing mechanism equalizes the vapor-content throughout chamber 12 and allows humidity sensor 50 to "see" the water molecules that were vaporized from the residual water. Accordingly, despite the notion among those skilled in the art that humidity sensors and humidity data derived therefrom do not enable accurate determinations of whether hydrogen peroxide should be introduced into a chamber or whether a load-conditioning process should be attempted, it appears humidity sensors and humidity data derived therefrom are quite useful in this regard.

Experiments were performed demonstrating that changes in the moisture content within a vacuum chamber caused by residual water on sterilization loads may be detected using a relative humidity sensor. The experiments were performed using a modified STERRAD® 100NX® sterilization system, with an HIH-4602-A/C Series Relative Humidity sensor produced by Honeywell International, Inc. configured to read humidity within the 100NX's vacuum chamber. An isolation valve was disposed between the humidity sensor and the vacuum chamber to protect the humidity sensor from potential exposure to hydrogen peroxide.

Figure 2:
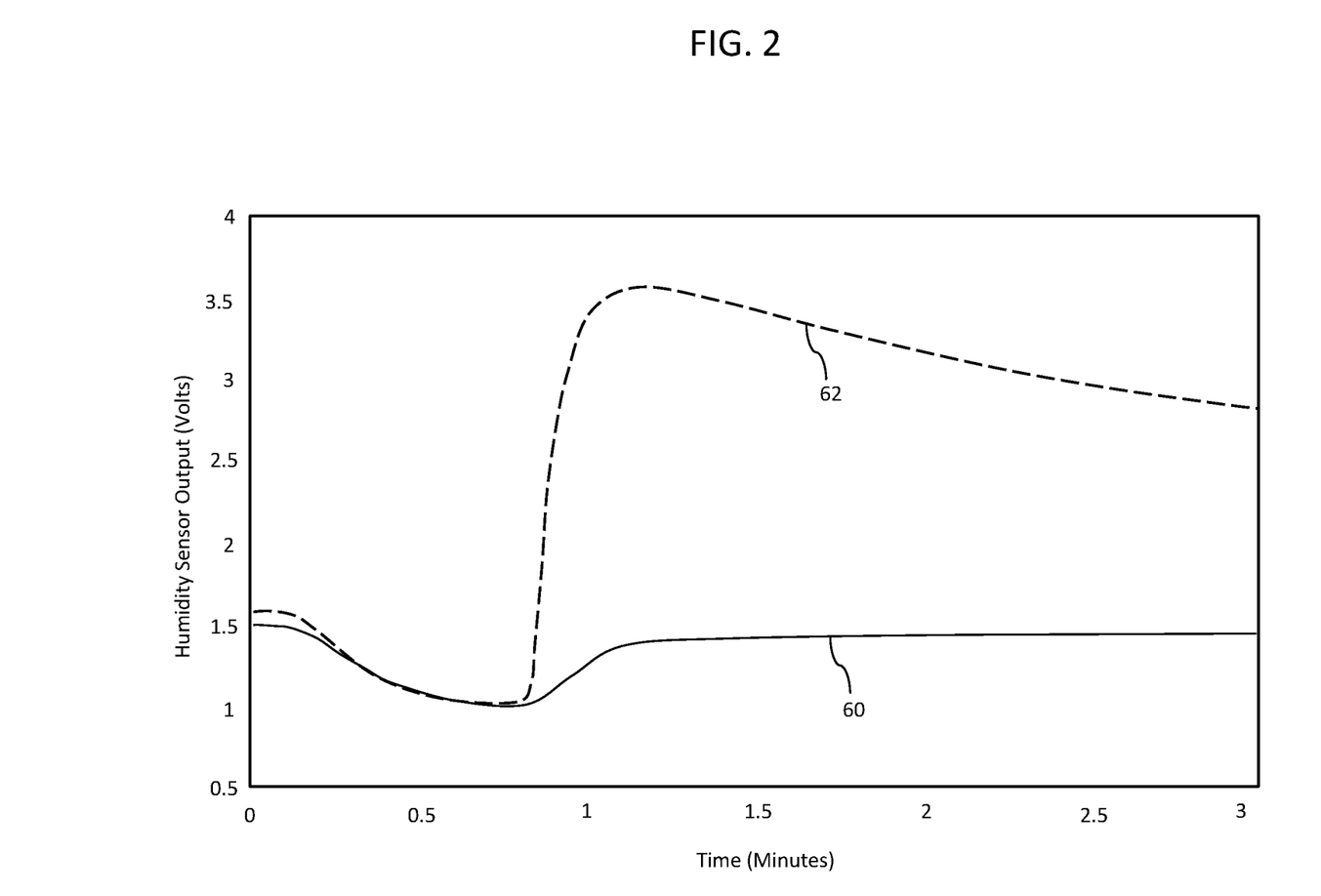
FIG. 2 is a graph plotting humidity-sensor output versus time for a wet load and a dry load within a vacuum chamber of a sterilization system like that depicted in FIG. 1.

Humidity data from one experiment are reflected in the graph of FIG. 2. The sterilization system used for this experiment was a 100NX® modified to include a humidity sensor capable or measuring humidity within the vacuum chamber. An isolation valve was placed between the humidity sensor and the vacuum chamber that could be closed to protect the sensor from any hydrogen peroxide that may be introduced into the vacuum chamber. The graph plots voltage output from the humidity sensor versus time. This experiment included two runs. In one run, a wet load containing approximately 5 ml of residual water was disposed in the vacuum chamber. In another run, a dry load was disposed in the vacuum chamber. Reference numeral 62 corresponds to the plot of humidity data for the wet load. Reference numeral 60 corresponds to the plot of humidity data for the dry load.

At t=0, while the pressure within the vacuum chamber was the ambient pressure and the ambient temperature was 18° C., the humidity was slightly higher for the wet load. That is, the humidity sensor output a voltage of approximately 1.6 volts for the wet load and approximately 1.5 volts for the dry load. Beginning at approximately t=0.15 minutes, the vacuum pump of the modified 100NX® began to purge air from the chamber. A notable drop in voltage output from the humidity sensor was observed, which is reflected from approximately t=0.15 minutes (corresponding to approximately ambient pressure) to approximately t=0.7 minutes (corresponding to approximately the conditioning pressure of 10 torr). During this period, the difference between the two plots of data disappears and the two plots overlap with each other beginning at approximately t=0.4 minutes. This overlap shows that data from the humidity sensor for wet loads and dry loads at lower pressures is similar. Accordingly, these data cannot be used to distinguish between wet loads and dry loads. This may be one reason why those of skill in the art may have believed humidity sensors should not be used to distinguish between wet loads and dry loads as a basis for determining whether hydrogen peroxide should be introduced into a vacuum chamber for sterilization.

Beginning at approximately t=0.7 minutes, the vacuum pump is deactivated and the vacuum-pump's valve is sealed to maintain pressure within the chamber until approximately t=0.8 minutes, which allows any residual water to continue vaporizing. Then, the modified 100NX® is vented and ambient air rushes into the vacuum chamber. For the dry load, by approximately t=1.5 minutes, the voltage output from the humidity sensor returns to approximately what it was at t=0. However, for the wet load, at approximately t=1.1 minutes, the voltage output from the humidity sensor has reached approximately 3.6 volts, which is approximately three times greater than the corresponding values for the wet load and dry load at t=0. Accordingly, whereas the voltage output from the humidity sensor before pressure in the chamber is lowered cannot be used to distinguish between wet loads and dry loads, there is a distinct difference between the wet and dry loads in the voltage output from the humidity sensor after pressure in the chamber has been lowered and the chamber vented.

Humidity data, such as the data reflected in FIG. 2, may thus be used as a basis for determining whether a load is sufficiently dry for hydrogen peroxide sterilization. For example, humidity values on a plot of humidity vs. time corresponding to times subsequent to venting, which may include the maximum humidity value on the plot, may be compared to the baseline value of humidity for a dry load, i.e., the humidity of an empty chamber or a chamber with a dry load disposed therein that was previously determined when the chamber was at ambient conditions. Alternatively, these humidity values may be compared to the minimum value of humidity on the humidity vs. time curve for empty chamber or a chamber with a dry load disposed therein that was previously determined when the pressure in the chamber was lowered to a condition pressure, such as approximately 10 torr. Alternatively, these humidity values may be compared to the baseline humidity value at t=0 and/or the minimum humidity value on the same plot because of the similarity of the humidity plots for wet loads and dry loads before the chamber is vented. Whichever type of comparison is performed, a marked difference between the humidity values before and after venting indicates that a load contained residual water. In some exemplary comparisons, a maximum humidity value greater than the baseline humidity value is considered to indicate a wet load whereas a maximum humidity value equal to or less than the baseline humidity value is considered to indicate a dry load.

Figure 3:
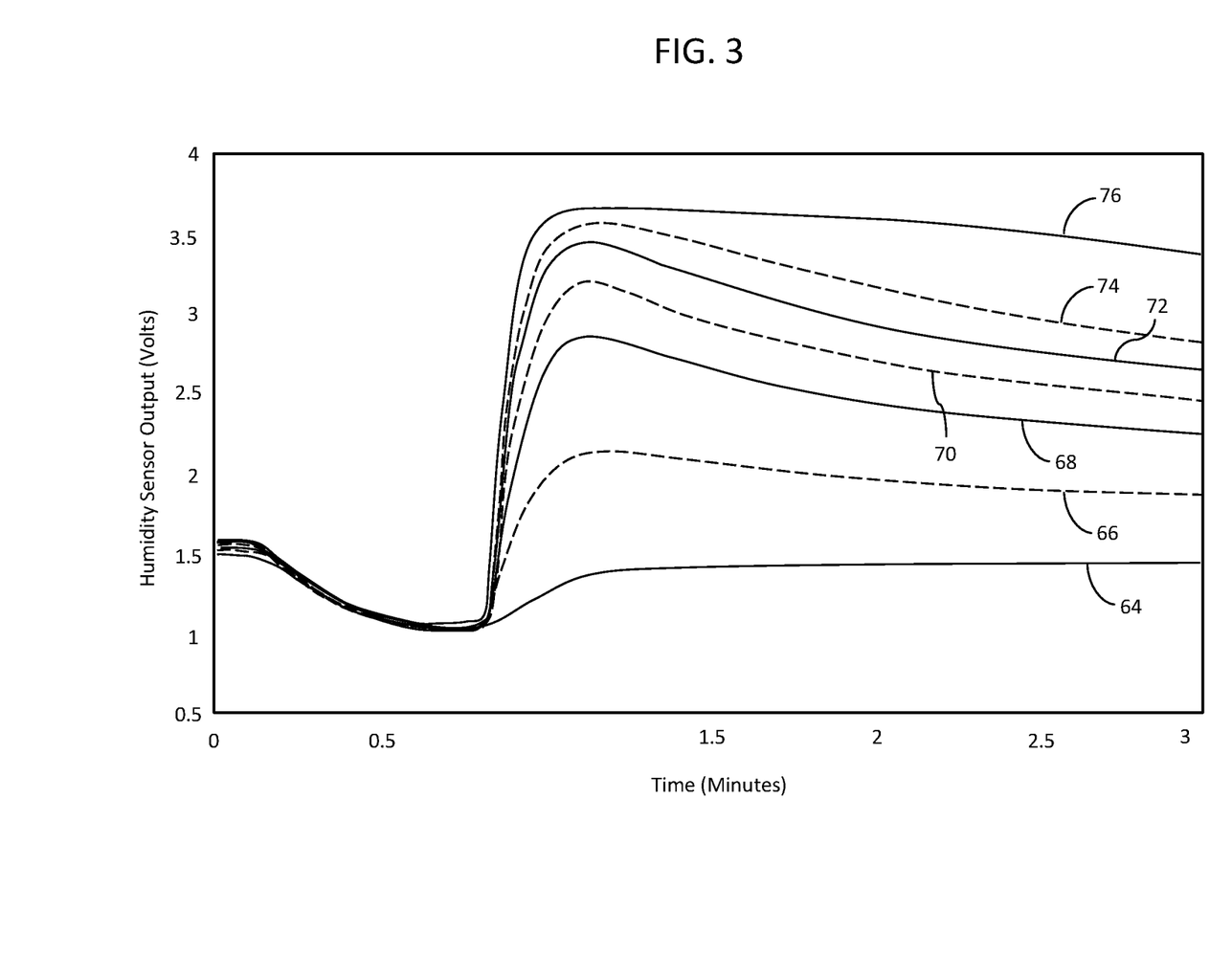
FIG. 3 is a graph plotting humidity-sensor output versus time for various wet loads and a dry load within a vacuum chamber of a sterilization system like that depicted in FIG. 1.

Further experiments were performed to correlate relative differences in humidity sensor outputs for maximum humidity values and baseline humidity values with known quantities of residual water within a load. These correlations may then be used to estimate the amount of residual water in other loads in the future. These data are reflected in FIG. 3. Reference numeral 64 corresponds to a dry load. Reference numeral 66 corresponds to a load with approximately 1 mL of residual water disposed thereon. Reference numeral 68 corresponds to a load with approximately 2 mL of residual water disposed thereon. Reference numeral 70 corresponds to a load with approximately 3 mL of residual water disposed thereon. Reference numeral 72 corresponds to a load with approximately 4 mL of residual water disposed thereon. Reference numeral 74 corresponds to a load with approximately 5 mL of residual water disposed thereon. Reference numeral 76 corresponds to a load with approximately 10 mL of residual water disposed thereon. For each set of data, the baseline humidity at t=0 is similar, i.e., between approximately 1.5 and approximately 1.6 volts. The pressure in the chamber starts being lowered at approximately t=0.15 minutes, and a corresponding drop in humidity for each curve is observed. By around approximately t=0.4 minutes, the humidity values for each sample begin overlapping or approximately overlapping. That is, the humidity values for each sample, from the dry sample to the wettest 10 ml sample, are equal or approximately equal. At approximately t=0.7 minutes, the chamber is sealed, at which point the humidity output for each sample is approximately 1.1 volts, the minimum humidity value for each curve. An increase in the humidity values is immediately thereafter observed on the 10 ml curve (reference numeral 76). The chamber is vented at approximately t=0.8 minutes. By approximately t=1 minute, the humidity vs. time curves have each diverged from the others. Then, by approximately t=1.1 minutes to approximately t=1.15 each of the humidity vs. time curves corresponding to the wet loads has have reached their maximum humidity values. For the 10 ml curve, reference numeral 76, the maximum humidity value is approximately 3.7 volts. For the 5 ml curve, reference numeral 74, the maximum humidity value is approximately 3.6 volts. For the 4 ml curve, reference numeral 72, the maximum humidity value is approximately 3.4 volts. For the 3 ml curve, reference numeral 70, the maximum humidity value is approximately 3.2 volts. For the 2 ml curve, reference numeral 68, the maximum humidity value is approximately 2.8 volts. For the 1 ml curve, reference numeral 66, the maximum humidity value is approximately 2.2 volts. For the dry curve, reference numeral 64, the humidity values reach approximately 1.4 volts, which is less than the baseline humidity value. These data may be used to determine the amount of moisture introduced into the vacuum chamber in the future. For example, if the maximum humidity value of a load is approximately 3.5 volts, it may be determined that the load included approximately 4 ml to 5 ml of residual water. Alternatively, the data suggest that if the maximum humidity value is approximately 0.5 volts to 0.75 volts greater than the baseline humidity value, or approximately 1.0 volts to 1.25 volts greater than the minimum humidity value, the load may be too wet to sterilize reliably with hydrogen peroxide. Accordingly, these data may be used as a basis for determining that hydrogen peroxide should not be introduced into the vacuum chamber until after the load has been dried, either manually or via a load conditioning process. However, if the maximum humidity value of a load is approximately equal to or less than the baseline humidity value of approximately 1.5 volts, then the load may be sufficiently dry for sterilization by hydrogen peroxide. Accordingly, these data may be used as basis for determining that hydrogen peroxide may be introduced into the vacuum chamber for sterilization.

Further experiments were performed that confirmed that the above described experiments are repeatable and provide reliable results.

III. Load Conditioning

In some instances, residual water within a load may be removed from a vacuum chamber by a process called "load conditioning." The technology described above may be incorporated into a load conditioning process to help determine whether the load conditioning process is drying a load as intended and, ultimately, whether the load is sufficiently dry for sterilization by hydrogen peroxide. One technique of load conditioning is sometimes referred to as "vacuum pulsing." Vacuum pulsing typically begins when a vacuum chamber is in a low pressure state and includes some combination of providing energy to a load in the chamber, pressurizing the chamber, and reducing the pressure. Building on the techniques set forth above, for example, air may be withdrawn from a vacuum chamber containing a wet load having, e.g., 5 ml of water therein until the pressure within the chamber reaches a conditioning pressure, $P_c$, of approximately 10 torr. Following a dwell time during which the conditioning pressure is maintained, the chamber may be vented. The venting should cause the humidity sensor to output a maximum humidity value of approximately 3.6 volts, based on the foregoing description concerning FIGS. 2-3. Before venting, energy may be provided to the load by way of a plasma or by using heating elements, such as heating elements 26 to further exacerbate vaporization of any residual water. Alternatively or additionally, the chamber may be vented to introduce ambient air into the chamber that is warmer than the air presently in the chamber, which may warm the load and residual water thereon. At this point, there should be less than 5 ml of residual water disposed within the load because at least some of the residual water should have been vaporized during the foregoing steps, which is what causes the maximum humidity value to be greater than the baseline humidity value. However, some residual water may remain. Again, air may be withdrawn from the chamber, and perhaps energized, before the chamber is vented again. Output from the humidity sensor should indicate that some water remained, but that the amount of water that remained is less than the original 5 ml. These steps may be repeated multiple times until the output from the humidity sensor is less than the baseline humidity value.

Figure 4:
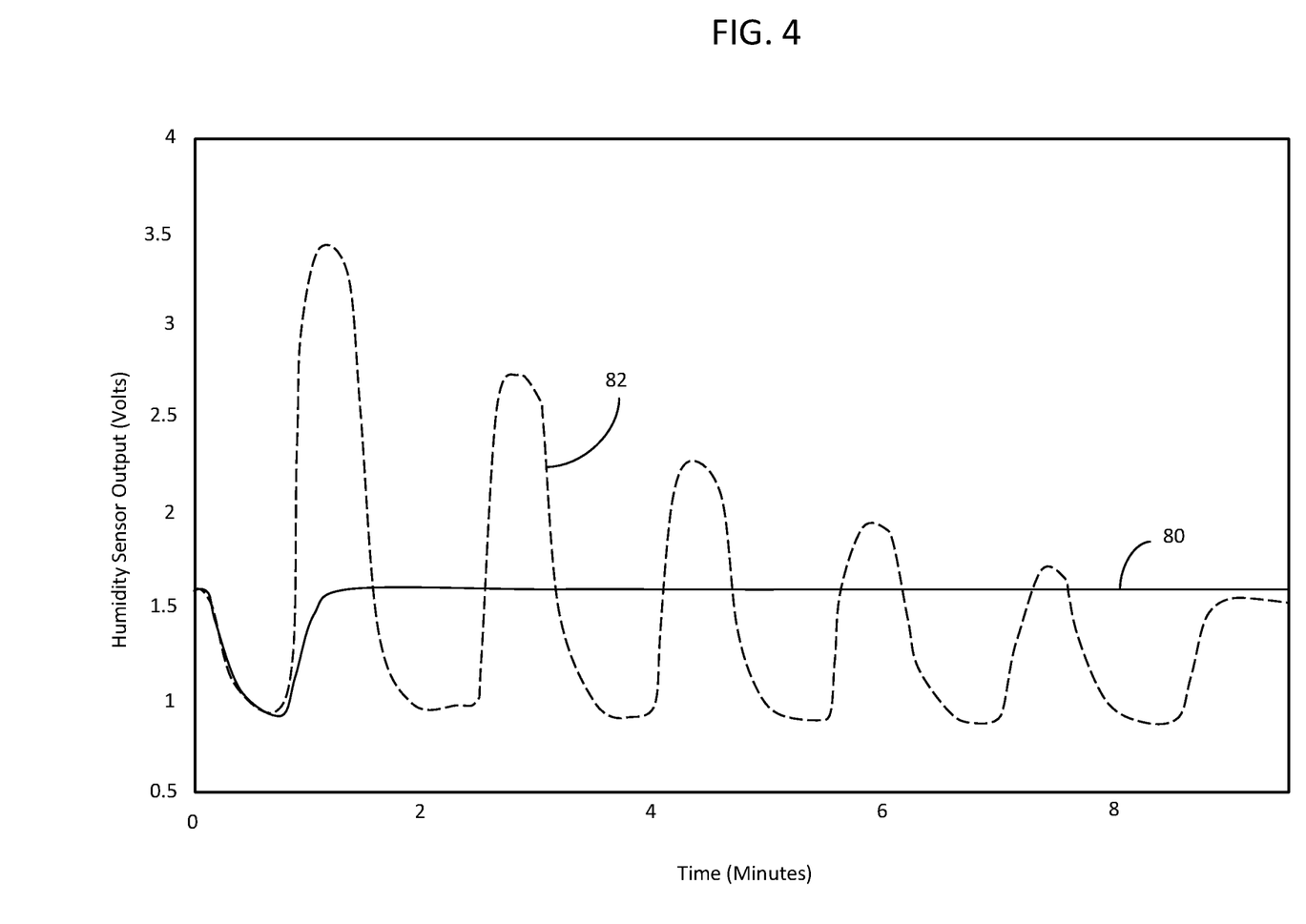
FIG. 4 is a graph plotting humidity-sensor output versus time for a wet load subjected to a load conditioning process and a dry load within a vacuum chamber of a sterilization system like that depicted in FIG. 1.

Data from a vacuum pulsing process is reflected in FIG. 4. A plot of data corresponding to humidity vs. time for a wet load containing 5 ml of water that is subject to vacuum pulsing is indicated by reference numeral 82. A plot of data corresponding to humidity vs. time for a dry load is indicated by reference numeral 80. The load conditioning process for the wet load begins in a manner similar to the process described in conjunction with FIG. 2. The first maximum humidity value occurs at approximately time t=1.1 minutes. The first maximum humidity value is approximately equal to 3.4 volts, close to the corresponding value of approximately 3.6 volts in FIG. 2. Air is then repeatedly withdrawn to a conditioning pressure, $P_c$, which may be approximately equal to 10 torr, and subsequently reintroduced into the chamber by venting the chamber, thereby energizing any water that remains therein. Following each venting step, the maximum humidity value is compared to the baseline humidity value to determine if the load was dry. If it is not dry, the vacuum pulsing continues until the maximum humidity value is less than or equal to the baseline value. As shown in FIG. 4, the sample load having 5 ml of residual water therein was determined to be successfully dried via load conditioning following six venting steps.

IV. Sterilization System Routines

A low-temperature chemical sterilization system, such as sterilization system 10, may be designed to perform various routines concerning determining whether any water is in vacuum chamber 12, whether load conditioning should be performed, and whether hydrogen peroxide should be introduced into the vacuum chamber. An example sterilization process, which includes steps that a sterilization system may perform, such as a routine for determining whether load conditioning should be performed, a load conditioning routine, and a sterilization routine, as well as other steps that a healthcare worker may perform, is set forth in FIG. 5. This process is set forth only as an example to further illustrate the disclosed subject matter and explain its utility. Many of the steps included in this process may be performed alternatively or additionally before or after other steps. The steps set forth in this example may be performed in varying combinations and permutations without departing from the scope of the disclosed subject matter. For example, load conditioning routines may be performed and/or air plasma introduced into the vacuum chamber before any steriliant is introduced into the vacuum chamber.

Figure 5:
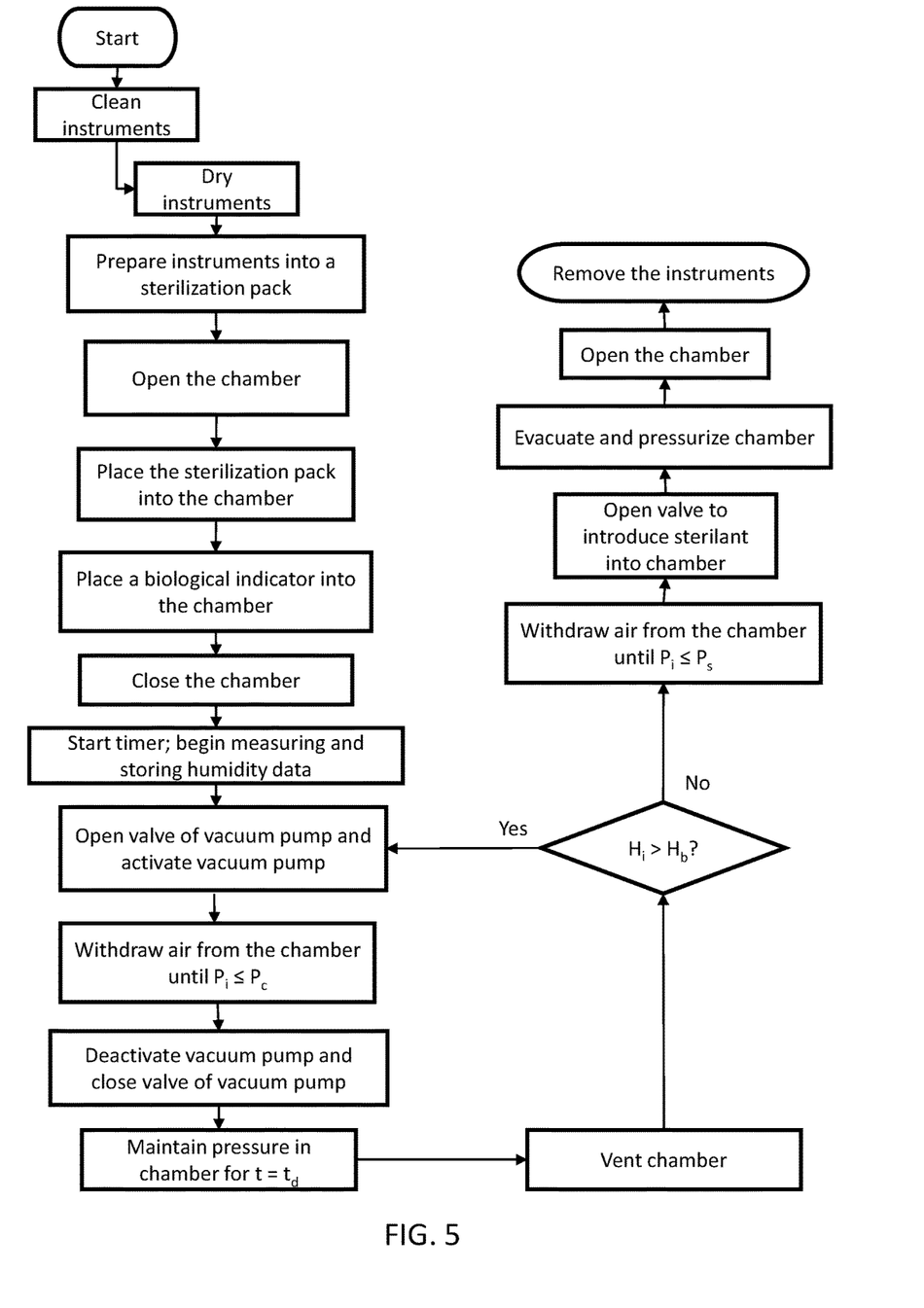
FIG. 5 is a flow diagram of an exemplary method for using a sterilization system.

As detailed in FIG. 5, the example sterilization process begins with health care personnel cleaning non-sterile instruments soiled from prior use using water, washing solution, or a water-soluble instrument lubricant. The instruments are then dried using any or a combination of various techniques known in the art, such as heating the instruments or blowing compressed air into the instruments, particularly lumens of the instrument. The dried instruments may be placed within a sterilization box or rack made from, e.g., a metal, such as aluminum, or a plastic, such as polycarbonate. The instruments and/or rack are wrapped within a sterilization wrap to form sterilization pack or load 14. The wrap acts as a barrier to microorganisms, but it permits passage of a steriliant therethrough. Once wrapped, the pack is ready to be introduced into the vacuum chamber 12 of sterilization system 10. A biological indicator may also be disposed within the chamber. The chamber is closed and sealed by closing barrier 16. At this point, timer 45 is started and control system 38 begins recording humidity data output from humidity sensor 50 at each time increment $\Delta t$, which may be every approximately 0.1 seconds or approximately 1 second. The first humidity data point recorded, which corresponds to time $t=0$ and the original pressure in the chamber, which may be equivalent to the ambient pressure, is the baseline humidity value, $H_b$. Valve 22 of vacuum pump 18 is opened and vacuum pump 18 is activated. Air is withdrawn from chamber 12 by pump 18 until pressure sensor 24 indicates that the pressure in chamber 12 is less than or equal to a predetermined conditioning pressure, $P_c$. $P_c$ may be any pressure at which water becomes readily vaporized, for example, approximately 10 torr. Once the pressure in chamber 12 reaches $P_c$, pump 18 is deactivated and valve 22 is closed. The pressure in chamber 12 is maintained at $P_c$ for a period of time, or dwell time, $t_d$, which may be equal to approximately 0.1 seconds, approximately 0.5 seconds, approximately 1 second, approximately 5 seconds or approximately 10 seconds. Following $t_d$, chamber 12 is vented to atmosphere, perhaps by opening valve 22 without activating pump 18 and/or opening the venting valve. Control system 38 and particularly processor 40 check subsequent values of $H_i$ to determine whether any such values are greater than the baseline humidity value, $H_b$. In some versions of the process, processor 40 compares only the maximum value of $H_i$, i.e., $H_{max}$, to $H_b$. In other versions of the process, processor 40 compares $H_i$ and/or $H_{max}$ to the minimum value of $H_i$, i.e., $H_{min}$. If no $H_i$ is greater than $H_b$, and/or if $H_{max}$ is less than $H_b$, then it may be presumed that load 14 is dry. Accordingly, the sterilization cycle of the sterilization process may commence. Specifically, valve 22 is opened and pump 18 activated to withdraw more air from chamber 12 until a predetermined sterilization pressure, $P_s$, is achieved in chamber 12. $P_s$ may be approximately 0.3 torr, approximately 0.5 torr, approximately 1 torr, approximately 2 torr, or approximately 3 torr. Once the pressure in chamber 12 is at $P_s$, pump 18 is deactivated and valve 22 closed. An isolation valve between chamber 12 and sensor 50 should also be closed to prevent damaging sensor 50 with hydrogen peroxide. Valve 32 is open and hydrogen peroxide from sterilant reservoir 28 is introduced in vapor form, or a liquid form that readily vaporized (e.g., droplets), into chamber 12. Subsequently, chamber 12 is evacuated of hydrogen peroxide and pressurized back to, e.g., ambient pressure. The chamber is then opened by opening barrier 16. The instruments, now in a sterile state, may then be removed from within chamber 12.

If, however, an $H_i$ corresponding to a time after $P_c$ was achieved is greater than $H_b$, a load conditioning cycle may begin. In the process of FIG. 5, vacuum pulsing is performed by repeating the steps of withdrawing air from the chamber until the pressure has reached $P_c$, maintaining the pressure at $P_c$ for $t_d$, venting the chamber, and comparing subsequent $H_i$ to $H_b$. As before, if no $H_i$ is greater than $H_b$, and/or if $H_{max}$ is less than $H_b$, then it may be presumed that load 14 is dry. If this is not the case, then another round of load conditioning may be performed. Load conditioning may be repeated as many times as necessary to dry the load. Alternatively, the process may time out and abort if the load is not sufficiently dried within a certain number of conditioning attempts, such as 2, 5, 7, or 10 attempts.

It should be understood that any of the examples and/or embodiments described herein may include various other features and/or steps in addition to or in lieu of those described above. The teachings, expressions, embodiments, examples, etc. described herein should not be viewed in isolation relative to each other. Various suitable ways in which the teachings herein may be combined should be readily apparent to those of ordinary skill in the art in view of the teachings herein.

Having shown and described exemplary embodiments of the subject matter contained herein, further adaptations of the methods and systems described herein may be accomplished by appropriate modifications without departing from the scope of the claims. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

I claim:

1. A method of operating a sterilization system having a vacuum chamber for sterilizing instruments, comprising:
    (a) acquiring a baseline humidity measurement from within the chamber;
    (b) acquiring subsequent humidity measurements from within the chamber;
    (c) withdrawing a first volume of air from the chamber;
    (d) waiting for a dwell time after the first volume of air is withdrawn from the chamber;
    (e) introducing a second volume of air into the chamber after waiting for the dwell time;
    (f) identifying a maximum humidity measurement from among the subsequent humidity measurements; and
    (g) comparing the maximum humidity measurement to another humidity measurement.

2. The method of claim 1, wherein the another humidity measurement is the baseline humidity measurement.

3. The method of claim 2, wherein the step of acquiring the subsequent humidity measurements includes repeatedly taking humidity measurement data with a humidity sensor and storing the data in a non-transitory storage medium of a digital computer.

4. The method of claim 3, wherein the maximum humidity measurement is greater than the baseline humidity measurement.

5. The method of claim 4, further comprising commencing a sequence of vacuum pulsing.

6. The method of claim 3, wherein the maximum humidity measurement is less than or equal to the baseline humidity measurement.

7. The method of claim 6, further comprising introducing a sterilant into the chamber.

8. The method of claim 7, wherein the sterilant is hydrogen peroxide.

9. The method of claim 1, wherein the step of withdrawing a first volume of air from the chamber is performed until a first pressure within the chamber equals a conditioning pressure.

10. The method of claim 9, wherein the conditioning pressure is between approximately 5 torr and 15 torr.

11. The method of claim 10, wherein the conditioning pressure is approximately 10 torr.

12. The method of claim 1, wherein the dwell time is between approximately one second and approximately one minute.

13. The method of claim 12, wherein the dwell time is approximately five seconds.

14. The method of claim 1, further comprising identifying a minimum humidity measurement from among the subsequent humidity measurements.

15. The method of claim 14, wherein the another humidity measurement is the minimum humidity measurement.

16. The method of claim 15, further comprising determining that the maximum humidity measurement is approximately twice as large as the minimum humidity measurement.

17. The method of claim 16, further comprising commencing a sequence of vacuum pulsing.

\* \* \* \* \*